United States Patent [19]

Evans

[11] 4,060,404
[45] Nov. 29, 1977

[54] SELECTIVE HERBICIDE FOR SUGARCANE

[75] Inventor: Arlyn Wayne Evans, Memphis, Tenn.

[73] Assignee: E. I. Du Pont de Nemours and Company, Wilmington, Del.

[21] Appl. No.: 712,194

[22] Filed: Aug. 9, 1976

Related U.S. Application Data

[63] Continuation-in-part of Ser. No. 700,079, July 6, 1976, abandoned, which is a continuation of Ser. No. 607,896, Aug. 26, 1975, abandoned.

[51] Int. Cl.$^2$ .............................................. A01N 9/22
[52] U.S. Cl. ....................................... 71/93; 544/211
[58] Field of Search ............................................ 71/93

[56] References Cited

U.S. PATENT DOCUMENTS 3,873,540  3/1975  Fuchs et al. .......................... 260/248
3,902,887  9/1975  Lin ............................................ 71/93

OTHER PUBLICATIONS

Sund. Chem. Abst. vol. 73 (1970) 44182x.
Sund. Chem. Abst. vol. 64 (1966) 9974b.

*Primary Examiner*—Lewis Gotts
*Assistant Examiner*—Catherine L. Mills

[57] ABSTRACT

1-Methyl-3-cyclohexyl-6-dimethylamino-s-triazine-2,4(1H,3H)-dione.

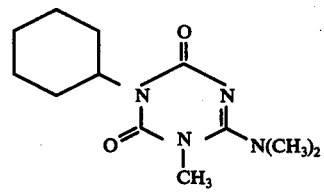

is useful for the selective control of many broadleaved and grassy weeds in sugarcane.

5 Claims, No Drawings

SELECTIVE HERBICIDE FOR SUGARCANE

CROSS-REFERENCE TO RELATED APPLICATIONS

This application is a continuation-in-part of copending application Ser. No. 700,079, filed July 6, 1976, now abandoned which in turn is a continuation of Ser. No. 607,896, filed Aug. 26, 1975, now abandoned.

BACKGROUND OF THE INVENTION

1-Methyl-3-cyclohexyl-6-dimethylamino-s-triazine-2,4(1H,3H)-dione and its use as a broad spectrum herbicide are disclosed and claimed in copending U.S. Patent application Ser. Nos. 476,553 now U.S. Pat. No. 3,983,116 and 476,552 now U.S. Pat. No. 3,902,887, both filed June 5, 1974, by Lin, both of which applications are divisions of U.S. Patent Application Ser. No. 348,321, filed Apr. 5, 1973, now abandoned, which is, in turn, a continuation-in-part of U.S. Patent Application Ser. No. 256,249, filed May 24, 1972 now abandoned.

The present invention results from the discovery that this compound exhibits a surprising selective herbicidal activity. That is, although this compound is known to be a potent broad-spectrum industrial herbicide, it has unexpectedly been found that this compound, when applied under the proper conditions, will effectively control many broadleaved and grassy weeds in sugarcane crops with safety to the crop.

SUMMARY OF THE INVENTION

This invention relates to the use of 1-methyl-3-cyclohexyl-6-dimethylamino-s-triazine-2,4(1H,3H)dione

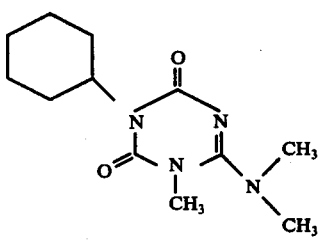

I as a selective herbicide in sugarcane. This compound can be applied either pre-emergence or post-emergence to effectively control a variety of broadleaved and grassy weeds in sugarcane with safety to the crop, i.e., application can be made pre-emergence to plant and stubble cane or as a directed post-emergence application after top growth is well started.

DESCRIPTION OF THE INVENTION

Synthesis of the compounds

The compound of formula I can be made by the processes described and exemplified in U.S. Pat. application Nos. 476,553 and 476,552, identified above, and by the process described and exemplified in U.S. Pat. No. 3,850,924 granted November 26, 1974 to Julius Fuchs and Joel B. Wommack.

In addition, the following preferred process, which is the subject of copending U.S. Patent Application Ser. No. 574,351, filed June 5, 1975 by Adams et al., now abandoned can be used to prepare the compound of formula I: Equation I represents preparation of the starting material as described in U.S. Pat. No. 3,657,443.

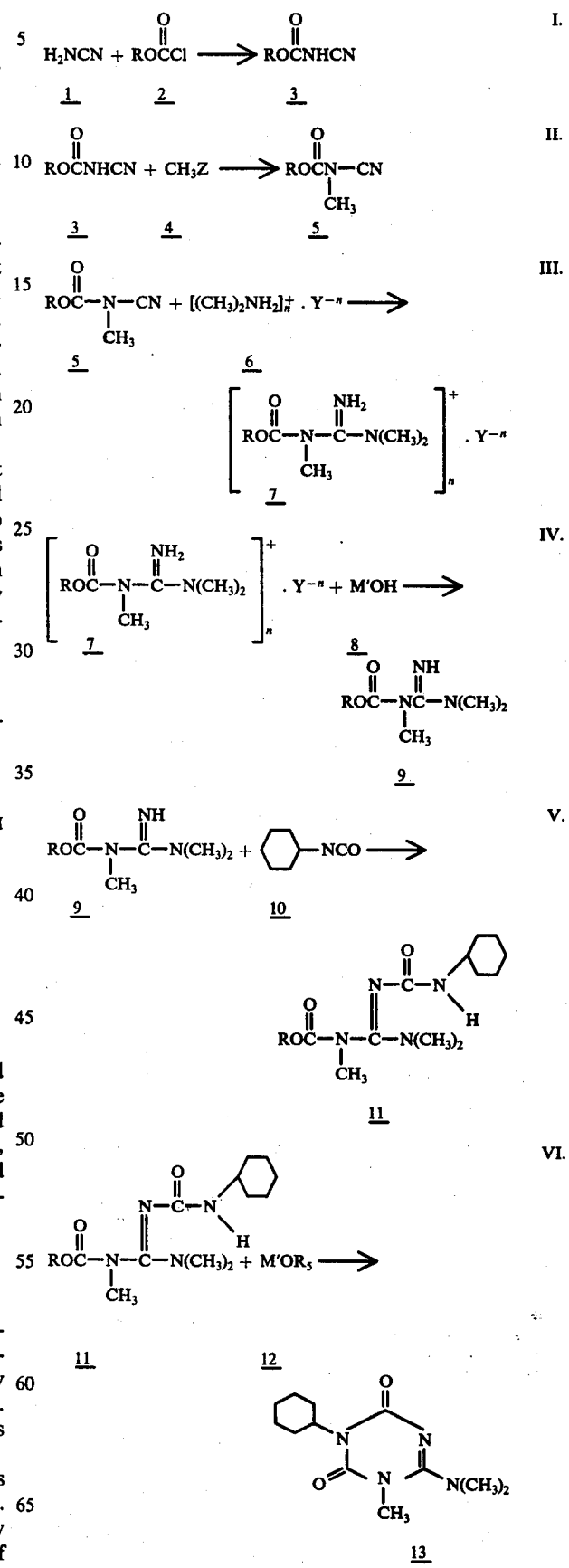

wherein
  R is ethyl, n-propyl, or isopropyl:
  Y is Cl− or SO$_4$=; $n = 1$ when Y is Cl− and $n = 2$ when Y is SO$_4$=;
  Z is iodide, bromide or

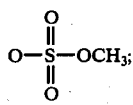

M' is alkali metal; and
  R$_5$ is hydrogen or alkyl of 1-4 carbon atoms.

Step I and II are performed sequentially in water. Compound 5 is isolated by separating it from the aqueous brine formed in these reactions.

After the reaction of step III is completed, compound 7 and any unreacted compound 6 must be converted to the free base forms with an alkali metal hydroxide. The untreated amine, (CH$_3$)$_2$NH, must be removed so that it will not be present in step V.

In the following detailed description, all temperatures are in degrees centigrade and all percentages are by weight unless otherwise stated.

An aqueous solution of the sodium salt of compound 3 containing from 15–35% of compound 3, preferably 20–30%, is reacted at 10°–70°, preferably 40°–45°, with 0.9–2.0, preferably 1.45–1.55 molecular equivalents of an alkylating agent 4 (for example, dimethyl sulfate) during a period of 1–16 hours, preferably 2–4 hours (equation II). Methyl iodide or bromide can be used instead of dimethyl sulfate; the sulfate is preferred for economic reasons.

As the reaction proceeds, a second phase of compound 5 forms. After the reaction has proceeded for the desired time, the upper layer is separated and the lower, aqueous, layer can be discarded, or if economic conditions justify, this layer can be extracted with an organic solvent, preferably toluene, or distilled to recover the small amount of compound 5 contained therein.

The upper layer is added to an aqueous solution containing 15–75% of the amine hydrochloride or 15–45% of the amine sulfate, compound 6, preferably 25–50% of the hydrochloride (equation III). The mole ratio of amine salt to compound 5 can be from 0.8–3, preferably 1.0–1.35. The mixture is then agitated for 0.5–6 hours at 50°–100°, preferably 85°–95° (equation III). Higher temperatures require shorter reaction time and vice versa. It is important to control the pH between 5.8 and 8.0 during reaction III. If the pH is too low, the reaction will be very slow; if the pH is too high, the product 7 will decompose. This control is most conveniently maintained by using electrodes to monitor the pH and adding base, for example, sodium hydroxide, potassium hydroxide, or calcium hydroxide as needed. Sodium hydroxide is preferred.

It should be realized that in these highly concentrated solutions, pH readings may be only coincidentially related to the hydrogen ion concentration. However, when the meters and electrodes are calibrated against a standard buffer before use, the pH response of the electrodes in the reaction mass indicates the state of the reaction.

The resulting reaction mass contains compound 7 and by-product tri-substituted guanidine as well as unreacted compound 6, all present as salts. Before proceeding with step V it is necessary to convert compound 7 into its free base, compound 9. This also converts unreacted compound 6 into free amine, (CH$_3$)$_2$NH which is removed to prevent the formation of by-product ureas. This operation can be effected by adding 10–50% aqueous sodium hydroxide until the pH is 11.0 to 12.5 as determined by a glass electrode meter combination and extracting with an organic solvent. Distillation of a portion of the organic solvent used for extraction removes the more volatile amine, (CH$_3$)$_2$NH. The amine can also be removed directly from the aqueous alkaline solution by distillation. The former procedure is preferred.

The extraction procedure can be performed by passing the aqueous alkaline solution through a continuous counter-current extractor where the organic phase is a solvent such as methylene chloride, benzene, chlorobenzene, toluene, or xylene; toluene is preferred. A batchwise extraction can also be performed. Temperature can vary between 9° C. and 65° C. The amount of solvent can vary from 0.5 to 10 parts per part aqueous phase, depending on economic factors. The exit organic solvent is sent to a still where amine, (CH$_3$)$_2$NH, and any entrained water are distilled overhead, leaving a residual solution of compound 9. The concentration of compound 9 will, of course, depend on the operating parameters of the extractor and still.

The residual solution of compound 9 is analyzed by gas chromatography for tri-substituted guanidine and for compound 9. If any guanidine is present, a stoichiometric amount of 5–10% aqueous sulfuric or hydrochloric acid, preferably sulfuric, is added to form the salt of the guanidine.

Isocyanate 10 is now added. The amount added can vary from 0.8 to 1.0 moles of compound 10 per mole of compound 9; 0.90–0.98 is preferred. The resulting reaction mass is stirred at 10°–90° C., preferably 50°–75° C., until the reaction is complete. Reaction time can be from 0.5 to 8 hours.

If less than a stoichiometric amount of compound 10 has been added, the pH is adjusted to 5.5 by adding 5–10% sulfuric or hydrochloric acid; sulfuric is preferred. If acid has been added, the mixture is allowed to settle, and the layers are separated. The lower, aqueous, layer is recycled to the extraction step, and the upper layer is dried by distilling until a constant head temperature is attained either under vacuum or at atmosheric pressure; absolute pressure of 100 to 400 mm Hg is preferred.

If acid is not used, the reaction mass does not have to be distilled. The product 11 can be isolated by concentration and/or cooling of the solution until crystallization occurs followed by filtration or centrifugation. However, it is usually more convenient to carry it forward as a solution to the next step (equation VI).

Compound 9 is subject to decomposition in aqueous solution, particularly under conditions of high temperature and pH. Under such conditions it tends to decompose into the corresponding tri-substituted guanidine as illustrated in the following equation:

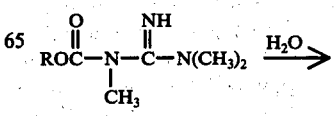

-continued

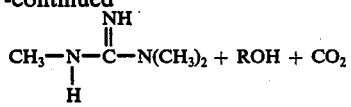

The rate of decomposition is directly proportional to the pH and temperature. Therefore, when removing amine, $(CH_3)_2NH$, by direct distillation from water, it is preferred to use a vacuum or inert gas to perform the operation as rapidly as possible.

The above-mentioned aqueous distillation procedure can be operated batch-wise or continuously. It is preferred to carry out the operation in a continuous manner so that the exposure of compound 9 to high temperature and high pH is reduced to a minimum. This is accomplished by adding aqueous alkali metal hydroxide to the product from step III in a pipeline reactor or by running the product and an alkali metal hydroxide into a small agitation vessel with a short hold-up time, no more than 10, preferably no more than 2 minutes. The separate flow rates are adjusted so that the resulting pH is between 11.0 and 13.0. If the concentration of amine salt used is such that alkali metal salt precipitates during this neutralization, additional water should be added to maintain this salt in solution. The overflow from this vessel is fed through a distillation column operated under vacuum. The column is heated by feeding steam into the bottom. Amine, $(CH_3)_2NH$, and water are taken off as distillate overhead and an aqueous solution of compound 9 and tri-substituted guanidine as bottoms.

The conditions under which the column can be operated are selected so that the temperature of the feed through the column is not over 50° C. This necessitates cooling the product from equation III to approximately 30° C before adding the caustic. The column is operated at an absolute pressure of 25-300 mm of mercury, preferably 50-150 mm, and the amount of steam fed to the bottom of the column is adjusted such that the amount of water taken overhead along with the amine is equivalent to 5-25% of the weight of the reaction mass from equation IV.

The bottoms from the above distillation are fed into a hold tank which is maintained at a pH of 5-7 by the continuous addition of either sulfuric or hydrochloric acid; hydrochloric is preferred. The concentration of compound 9 in the neutralized solution is maintained at 15-50%, preferably 20-40%. The concentration will depend upon the concentration of the aqueous solution of the amine, the concentration of the base and acid solutions employed in the previous steps, and the amount of concentration or dilution which occurred during the distillation. The temperature of this solution is maintained at 25-45°, preferably 25°-35°, by either cooling the bottoms in a continuous-type cooler before neutralization or by cooling the neutralization vessel itself.

When the amine has been removed by direct distillation from water, step V is performed by preparing a mixture of the above solution and a solvent such as benzene, chlorobenzene, toluene, or xylene; toluene is preferred. The amount of solvent added should be sufficient to dissolve the amount of compound 11 which will be formed. Generally, the amount of solvent used is about 7-10 times the amount of compound 11 present in the aqueous solution.

An amount of compound 10 which is stoichiometrically equivalent to 85-100%, preferably 90-98%, of compound 9 present in the aqueous layer is now added in one portion or continuously for up to three hours, preferably 30 minutes to one hour and 50% aqueous caustic is added simultaneously with good agitation at a rate which will maintain the pH at 9-10, preferably 9.3-9.7. The caustic addition is continued until the pH is almost constant. The temperature is maintained at 10°-90° C., preferably 35°-50° C., during the addition by external heating and cooling as required. The caustic addition time is from 1-8 hours. The pH is then adjusted to 6.0 with acid. The agitation is stopped and the layers allowed to separate. The lower aqueous layer is removed and the upper organic layer is dried by distilling until a constant head temperature is attained either under vacuum or at atmospheric pressure; absolute pressure of 100-400 mm Hg is preferred.

The solution or slurry containing compound 11 is cooled if necessary to 25°-55° C while anhydrous free dimethylamine is added. It is preferred to add the amine at 25°-55° C, but higher or lower temperatures can be used depending on the solubility of the amine in the particular solvent. It is important to have at least 0.5, and preferably 1.0-8.0 moles of amine per mole of compound 11.

Next the ring closure catalyst (compound 12) is added (equation VI). The catalyst is an alkali metal alkoxide or hydroxide. Alkali metal alkoxides can be added either as dry solid or as a solution in the alkanol. Alkali metal hydroxides can be added as a solution in an alkanol. Dry sodium methoxide or a solution of sodium methoxide in methanol is a preferred catalyst. The amount of catalyst needed is from 0.1 to 5.0 mole percent of compound 11. Higher concentrations are not desirable because side reactions begin to intervene. A preferred concentration of compound 12 is from 2.0 to 4.0 mole percent of compound 11. The temperature is not critical and the ring closure reaction can proceed at temperatures from 0° to 120° provided that the amine is kept within the reaction system. The reaction is normally exothermic and the solution may be cooled if a lower temperature is required to retain the amine. It is critical that the amine remain present until ring closure is about complete.

After the catalyst is added, the reaction mass is held for 15 seconds to 2 hours to insure completion of the ring closure. The reaction is rapid and normally is about complete in less than 15 minutes. The more completely anhydrous the reaction mass, the more rapid is the reaction. An amount of acid equivalent in moles to the amount of the catalyst is added to the reaction mass after ring-closure is complete. This acid neutralizes the catalyst and/or reaction by-products which catalyze product decomposition during the isolation step. Preferably, the acid is added as soon as possible after ring-closure is complete. The type of acid, either organic or inorganic, is not critical; but organic acids are preferred, particularly acetic acid. The added amine, by-product alkanols, and part of the solvent are then removed by distillation either at atmospheric or reduced pressure.

Alternatively, the ring-closure reaction can be performed in a continuous manner. In this embodiment the catalyst is mixed with the reaction mass containing compound 11 and the amine in a pipeline reactor. The acid is added downstream after the temperature rise is complete. The amine, by-product alcohols and part of the solvent are then removed by distillation.

The residue is washed at 30°-100° C., preferably 50°-70° C., with 5% aqueous alkali metal hydroxide, preferably sodiumm hydroxide, in an amount equal to or slightly greater than (up to 20% molar excess) the amount of catalyst. The layers are allowed to settle, the aqueous layer is removed, and the organic layer is washed with water in an amount approximately equivalent in volume to the caustic wash. Again the layers are allowed to settle, the aqueous layer is removed, and the pH of the wet organic layer is adjusted to 6–7 with acid. (The pH is measured using a glass-calomel combination electrode.) Organic acids are preferred for this operation; acetic acid is especially preferred. This washing procedure removes by-products formed during the ring-closure reaction. If a less pure product is satisfactory, the washing steps can be eliminated.

The product can be isolated from the organic solvent, either after the washing operation or without washing, through concentration of the organic phase by distillation. The concentrate is then diluted with a poor solvent for compound 13, e.g., hexane, which causes compound 13 to precipitate. The stable crystalline product is recovered by conventional methods.

In the following examples, all parts are by weight and all temperatures in degrees centigrade unless otherwise indicated.

EXAMPLE 1

A. Synthesis N-ethoxycarbonyl-N-methylcyanamide (Equations I and II)

657 Parts of ethyl chloroformate and 945 parts of a 50% aqueous sodium hydroxide solution were added simultaneously to a solution of 504 parts of a 50% aqueous cyanamide solution in 825 parts of water at 25° during a period of 90 minutes and at a pH of 6.9 to 7.1. As the addition of the reactants progressed, the temperature of the reaction mass was allowed to rise to 53°–55° and was maintained within that range by cooling. When the addition was comlete, the reaction mass was cooled to 40°. Dimethylsulfate (1,134 parts) was then added during one hour with stirring while maintaining the pH at 7 to 7.1 by the addition of 50% aqueous sodium hydroxide solution. After holding 3 hours at 40° the resulting two-phase solution was transferred to a separatory funnel. The upper phase of N-ethoxycarbonyl-N-methylcyanamide was separated and the lower aqueous phase was sent to secondary recovery, either distillation or extraction. The upper phase of 669 parts was 93% N-ethoxycarbonyl-N-methylcyanamide (81% yield). This upper phase is usually pure enough for subsequent steps. However, vacuum distillation was used to provide pure N-ethoxycarbonyl-N-methylcyanamide, b.p. 67° at 2.2 mm.Hg.

B. Synthesis of N-ethoxycarbonyl-N,N',N'-trimethylguanidine (Equations III and IV)

A solution of 339 parts of dimethylamine hydrochloride in 500 parts of water was heated to 50° and 458 parts of the upper phase from (A) was added to it. The resulting two-phase mixture was then heated for approximately 2.25 hours at 90° and pH of 6.5, after which time the starting N-ethoxycarbonyl-N-methylcyanamide had nearly completely disappeared. The pH was kept at 6.5 by adding 50% sodium hydroxide as required. The solution was then cooled to 40° and 25% aqueous sodium hydroxide solution was added to reach pH 11.5 Repeated extraction of the reaction solution with toluene and partial evaporation of the toluene gave a solution containing 489 parts of crude N-ethoxycarbonyl-N,N', N'-trimethylguanidine from which the pure product was isolated by distillation at 70°/0.3 mm.Hg.

C. Synthesis of Ethyl N-(N'-cyclohexylcarbamoyl-N,N-dimethylamidino)-N-methylcarbamate (Equation V)

11 Parts of cyclohexyl isocyanate was added to 16 parts of N-ethoxycarbonyl-N,N',N'-trimethylguanidine in 150 parts of toluene. The temperature was kept at 50° to 75° for 1.25 hours to complete reaction. The product, ethyl-N-(N-cyclohexylcarbamoyl-N',N'-dimethylamidino)-N-methyl-carbamate was isolated by crystallization, filtration, and drying, m.p. 97°–98°. Preferably, however, it is kept as a toluene solution carried forward as such to the next step (Equation V).

D. Synthesis of 1-methyl-3-cyclohexyl-6-dimethylamino-s-triazine-2,4(1H,3H)dione (Equations II, III, IV, V)

A 50% stoichiometric excess of dimethylsulfate (1234 parts) was added at 40° during 1 hour with agitation to 3141 parts of an aqueous solution containing 888 parts of the sodium salt of compound 3 (R = ethyl) which had been adjusted to pH 7 with 50% aqueous sodium hydroxide. The reaction was allowed to continue for three hours while the temperature was maintained at 40° by external heating or cooling and at pH 7 by the addition of 50% aqueous sodium hydroxide as required. During the reaction a separate phase of compound 5 (R = ethyl) was formed.

When the reaction was about complete, the agitation was stopped and the layers allowed to separate. The upper layer of 728 parts was 93% pure compound 5 (R = ethyl). It was separated and added to 1,200 parts of an aqueous solution containing 540 parts of dimethylammonium chloride. The resulting mixture was heated to 90° and stirred for 2.25 hours at pH 6.5. The pH was maintained at 6.5 by adding 50% sodium hydroxide as required. The solution was then fed into a mixing tee along with 25% aqueous sodium hydroxide. The separate feed rates were adjusted so that the effluent from the tee was kept at pH 11.0–11.5. The effluent from this vessel was fed into the top of a continuous counter-current extractor, which operates as a 5 theoretical plate column. Toluene was fed into the bottom of the column at a rate of 2.25 pounds of toluene per pound of aqueous feed. The toluene solution at the top of the column overflowed into an amine stripper.

In the stripper, excess dimethylamine, entrained water, and some toluene solvent were distilled overhead through a packed column. The residual toluene solution of 7743 parts contained 777 parts of compound 9 (R = ethyl). Analysis showed by-product 1,1,3-trimethylguanidine to be present in this residue, and a small amount of sulfuric acid solution was added to exactly neutralized all the 1,1,3-trimethylguanidine but little or none of compound 9.

507 Parts of cyclohexylisocyanate was added to this residue. The mixture was then stirred at 50°–75° for 1.25 hours. It was cooled to 40° and sulfuric acid solution was added with good stirring until the pH of the aqueous phase was 5.5. The organic phase was separated and dried by brief azeotropic distillation at a pressure of 100 mm mercury. The organic phase of 8,200 parts contained 1,205 parts of compound 11 (R = ethyl).

Dimethylamine (1,095 parts) was added to the solution of compound 11 while the temperature was maintained at 25°–50° by external cooling. Then 35 parts of a 25% solution of sodium methoxide in methanol was added with good agitation. The reaction is slightly exothermic and the temperature increased 4° during 15–45 seconds. The reaction was allowed to continue for an additional two minutes; then 9.72 parts of acetic acid were added. The solution was then distilled until a constant 110° head temperature showed that dimethylamine and by-product alkanols have been completely removed. The still bottoms were cooled to 60° and washed with a small quantity of 5% hydroxide followed by a small quantity of water. The amount of sodium hydroxide was calculated so that it was equivalent in moles to the acetic acid added earlier.

The toluene phase was then concentrated by distillation until the concentration of compound 13 ($R_1$ = reached 50% by weight. The residue was cooled to 40° and stirred while n-hexane was added slowly.

The weight of n-hexane used was 80% of the total weight of the 50% solution. During the n-hexane addition the solution was seeded with compound 13. The crystals were recovered by filtration and dried to give 920 parts of compound 13 m.p. 112°–115° C.

Formulation and use of the compound

The compound of formula I is useful for control of undesired vegetation in sugarcane fields, i.e., the compound of formula I can be used to control a variety of broadleaves and grassy weeds in sugarcane fields with safety to the surgarcane plants.

The precise amount of compound to be used in any given situation will vary according to the time of treatment, the weed species and soil type involved, the formulation used, the mode of application, prevailing weather conditions, particularly rainfall, foliage density and like factors. In addition, sugarcane variety and age of planting should be taken into consideration.

Certain varieties of surgarcane, such as the Queensland varieties and most other shallow rooted varieties, for example 48-103 (Louisiana), 50-28 (Texas), 53-263 (Hawaii) and P. R. 1048 (Puerto Rico), are known to be susceptible to weed killers and may be injured at relatively low rates. Tolerance of such susceptible varieties to the compound of formula I under the particular field conditions in use should be determined by routine experimentation before adoption as field practice to prevent possible crop injury.

In any event, use rates necessary to provide effective control, even with respect to many weed species that are resistant to other herbicides, are quite low. Since so many variables play a role, it is not possible to state the rate of application suitable for all situation. However, broadly speaking, the compound of formula I is used at levels of about 0.25 kg/ha to about 4 kg/ha. The lower rate given here will provide only a brief effect on weeds under many use conditions. The higher rate, on the other hand, will be excessive and can cause crop injury except where soils have a high colloidal content, where the more resistant varieties and strains of cane are grown, or where the crop plants are well established (i.e. "stubble" or "ratoon" cane). The most preferred rate is in the range of about 0.5 to about 1 kg/ha.

The application may be made pre-emergence to the plant and stubble cane or as a directed post-emergence spray after top growth is well started. Applications may be broadcast (i.e., cover the entire surface of the field) or limited to only a portion such as a band over the row.

In all instances, the treatment should be applied uniformlly.

Proper application of this compound results in good control of many serious and troublesome weeds that may occur in sugarcane fields. Some of the many different weed species controlled are wild turnip (*Brassica campestris*), johnsongrass seedlings (*Sorghum halepense*), common ragweed (*Ambrosia artemisifolia*), common crabgrass (*Digitaria sanguinalis*), foxtail (*Setaria sp.*), pigweed (*Amaranthus sp.*), Florida beggarweed (*Desmodium tortuosum*), cocklebur (*Xanthium pennsylvanicum*), morningglory (*Ipomoea sp.*), carpetweed (*Mollugo verticillata*), smartweed (*Polygonum sp.*), goosegrass (*Eleusine indica*), curly dock (*Rumex crispus*), burning nettle (*Urtica urens*), common yarrow (*Achillea millefolium*), chicory (*Cichorium intybus*), guineagrass (*Panicium maximum*), torpedograss (*Panciun repens*), purslane (*Portulaca oleracea*), barnyardgrass (*Echinochloa crusgalli*), dallisgrass (*Paspalum dilatatum*), vaseygrass (*Paspalum urvillei*), catsear (*Hypochaeris sp.*), chickweed (*Stellaria media*), goldenrod (*Solidago sp.*), darnel (*Lolium temulentum*), smooth crabgrass (*Digitaria ichaemum*), coffee senna (*Cassia occidentalis*), lambsquarters (*Chenopodium album*), henbit (*Lamium amplexicaule*), crowfoot (*Ranunculus sp.*), wild euphorbia (*Euphorbia sp.*), *Ageratum conyzoides, Digitaria ciliaris, Synedrella vialis, Richardia brasiliensia, Dactyloctenium aegyptium, Eragrostis tenella*, and nutsedge (*Cyperus sp.*). Of particular interest is the high activity of the componnd of this invention on actively growing nutsedge.

The compound of formula I can be used for weed control in sugarcane either alone or in combination with other herbicides. An important function of the added herbicide is to prolong the period of weed control obtained. Compounds particularly effective for this purpose are diuron [3-(3,4-dichlorophenyl)-1,1-dimethylurea], bromacil [3-(secbutyl)-5-bromo-6-methyluracil], terbacil [3-tert-butyl-5-chloro-6-methyluracil], and metribuzin [4-amino-6-tert-butyl-3-methylthio-1,2,4-triazine-5-one]. The optimum ratio between the compound of Claim 1 and the additional herbicide can be readily determined by a person of ordinary skill in the art of weed control.

In addition, in the case of combinations of the compound of formula I with diuron, not only is the period of weed control extended, but also the diuron exerts a definite and significant safening effect on the compound of formula I with respect to its phytotoxicity on the sugarcane plants, thereby enabling the sugarcane plants to tolerate higher levels without significant injury. Naturally, higher levels of the compound of formula I permit better control of resistent weed species.

Combinations of diuron and the compound of formula I may be effectively used in ratios of from 1:1 to 8:1 (by weight), preferably 1:1 to 4:1 (by weight). The safening effect of diuron on the compound of formula I has been demonstrated in a number of field tests.

The compound of formula I can be formulated in the various ways which are conventional for herbicides of similar physical properties. Useful formulations include wettable and soluble powders, suspensions and solutions in solvents and oils, aqueous dispersions, dusts, granules, pellets, and high-strength compositions. Broadly speaking, these formulations consist essentially of about 1–99% by weight of herbicidally active material and at least one of a. about 0.2–20% by weight of surface active agent, and
b. about 5–99% by weight of solid or liquid diluent.

More specifically, the various types of formulations will generally contain these ingredients in the following approximate porportions:

|  | PERCENT BY WEIGHT | | |
| --- | --- | --- | --- |
|  | Herbicide | Diluent | Surfactant |
| Wettable Powders | 25–90 | 0–74 | 1–10 |
| Suspensions or Solutions | 5–50 | 40–95 | 0–10 |
| Aqueous Dispersions | 10–50 | 40–89 | 1–10 |
| Dusts | 1–25 | 70–99 | 0–5 |
| Granules and Pellets | 1–35 | 65–99 | 0–15 |
| High-Strength Compositions | 90–99 | 0–10 | 0–2 |

The manner of making and using such herbicidal formulations is described in numerous patents. See, for example, Luckenbaugh. U.S. Pat. No. 3,309,192; U.S. Pat. No. 3,235,357: Todd, U.S. Pat. No. 2,655,445; Hamm et al., U.S. Pat. No. 2,863,752; Scherer et al., U.S. Pat. No. 3,079,244, Gysin et al., U.S. Pat. No. 2,891,855; and Barrous, U.S. Pat. No. 2,642,354.

EXAMPLE II

Solution

| 1-methyl-3-cyclohexyl-6-dimethyl-amino-s-triazine-2,4(1H,3H)-dione | 25.5% |
| --- | --- |
| ethylene glycol monobutylether | 53.2% |
| ethanol | 8.1% |
| water | 13.2% |

The ingredients were combined, warmed and stirred to produce a solution which was subsequently extended with water for spraying.

EXAMPLE III

Wettable Powder

| 1-methyl-3-cyclohexyl-6-dimethyl-amino-s-triazine-2,4(1H,3H)-dione | 25% |
| --- | --- |
| diatomaceous earth | 71.5% |
| dioctyl sodium sulfosuccinate | 1.5% |
| low viscosity methyl cellulose | 2% |

The ingredients can then be thoroughly blended and passed through a hammer mill to produce particles mostly all below 100 microns.

EXAMPLE IV 1.5% Granule

| 1-methyl-3-cyclohexyl-6-dimethyl-amino-s-triazine-2,4-(1H,3H)-dione | 1.5% |
| --- | --- |
| Athapulgus clay granules | 98.5% |

The active ingredient was dissolved in an ethanolwater mixture and sprayed onto a bed of the clay granules rotating in a mixer. The granules were removed and dried in a vacuum oven prior to packaging.

EXAMPLE V

Water soluble Powder

| 1-methyl-3-cyclohexyl-6-dimethyl-amine-s-triazine-2,4(1H,3H)-dione | 94% |
| --- | --- |
| zeolex 7A | 3.8% |
| sugar | 1.0% |
| methocel F-50 | 1.0% |
| aerosol OT-B | .2% |

The ingredients were thoroughly blended and passed though a hammer mill to produce particles mostly below 100 microns.

The selective herbicidal activity of the compound of formula I in sugarcane crops has been tested many times under varied climate and soil conditions. While all of these tests were not equally successful (optimum weed control with minimum or zero phytotoxicity to the sugarcane), the following tests are considered representative in demonstrating selective herbicidal activity of the compound of formula I when used under appropriate conditions.

EXAMPLE VI

Sugarcane in Louisiana that had been planted in August was treated pre-emergence with 1-methyl-3-cyclohexyl-6-dimethylamino-s-triazine-2,4(1H,3H)dione at rates, of 1, 2, and 4 kg/ha. The soil type was Commerce silt loam and the sugarcane variety was CP-61-37. The effect of treatment was observed 170 days later (after nearly 70 cm. of rainfall). At this time, a weed population made up primarily of henbit (*Lamiumamplexicaule*), chickweed (*Stellaria sp.*) and annual grasses had been controlled at all rates without injury to the crop.

EXAMPLE VII

CL-54-378 variety of sugarcane was planted 7 inches deep in Willow-Elder muck soil in Florida on September 8. Six days later, pre-emergence applications of 1-methyl-3-cyclohexyl-6-dimethylamino-s-triazine-2,4(1H,3H)dione were made at rates of 0.5, 1 and 2 kg/ha. Weed control on February 1, the following year was 75, 83 and 99%, respectively, for the three rates. The weed population in untreated areas adjacent was made up largely of goosegrass (*Eleusine indica*), wandering jew (*Zebrina pendula*) and purslane (*Portulaca oleracea*). This weed control was obtained without injury to the crop.

EXAMPLE VIII

In Taiwan, 61 and 79% weed control was provided by 0.5 kg/ha of 1-methyl-3-cyclohexyl-6-dimethylamino-s-triazine-2,4(1H,3H)-dione in two separate tests. At a 1 kg/ha rate weed control in the two tests was 85 and 94%, respectively. The weeds controlled included torpedo grass (*Panicum repens*) and two species of *Digitaria*. Only trace effects upon the cane were noted at the 1 kg rate.

EXAMPLE IX

Application of 1-methyl-3-cyclohexyl-6-dimethylamino-s-triazine-2,4(1H,3H)-dione at rates of 0.5, 0.75, 1.0 and 2.0 kg/ha were made pre-emergence to recently planted sugarcane of the NCO-310 and CP-61-37 varieties at three separate locations in the Rio Grand Valley. In all cases, weed control was 90% or better 12 weeks after treatment. Rates up to and including 1 kg/ha has no adverse effect upon the sugarcane. The 2 kg rate was also safe on a loam soil but caused some chlorosis and stunting on sandy soil.

Similar applications made on the same cane varieties and in the same area but post-emergence to a ratoon crop also gave 90% weed control (for 3.5 months in this case) without crop injury. Combinations of the compound of this invention with terbacil and with metribuzin were included in these tests with excellent results.

EXAMPLE X

In South Africa, applications of 1-methyl-3-cyclohexyl-6-dimethylamino-s-triazine-2,4(1H,3H)-dione at rates of 1.5 and 3 kg/ha were made pre-emergence to cane on a clay soil with 1% organic matter. After 43 days, weed control was excellent at both rates with no adverse effect upon the cane.

EXAMPLE XI

Plots in a sugarcane field in Hawaii were treated with 1-methyl-3-cyclohexyl-6-dimethylamino-s-triazine-2,4(1H,3H)dione at rates of 1, 2, 4 and 8 kg/ha. Weed control was excellent at even the 1 kilo. rate through a 90 day period during which about 80 cm of rainfall was received. There was no injury to the cane at the 1 and 2 kilo. rates but evident damage at 4 and 8 kilo. Weeds controlled included the genera Ageratum, Setaria, Digitaria, Oxalis and Rhus. Additions of 2 kg/ha or more of diuron prolonged the weed control without contributing to cane injury.

EXAMPLE XII

In Louisana, 1-methyl-3-cyclohexyl-6-dimethylamino-s-triazine-2,4(1H,3H)-dione was applied post-emergence to sugar cane variety CP 52–68 stubble cane, in heavy clay soil, in March at rates of 0.5, 1.0, 2.0 and 4.0 lbs/acre. Thirty days after treatment, no phytotoxicity was observed at any rate. Raoul grass (*Rottboellia exaltata*) was controlled 50%, 78%, 93% and 99% respectively for each of the rates. A variety of of broadleaved weeds including mature Carolina Geranium and various unidentified broadleaved seedlings were controlled 73%, 91%, 92% and 95%, respectively. Seventy-five days after treatment, no significant phytotoxicity was observed at the two lower rates, an acceptable level of phytotoxicity was observed at the 2.0 lb. rate, and an unacceptable level of phytotoxicity was observed at the 4.0 lb. rate with 63%, 79%, 95% and 94% control of Raoul grass, respectively.

I claim:
1. Method for preventing and controlling undesired vegetation in sugarcane crops without causing significant injury to said crop comprising applying to the locus of said crop an effective amount of 1-methyl-3-cyclohexyl-6-dimethylamino-s-triazine-2,4(1H,3H)-dione.
2. Method of claim 1 wherein the triazine is applied at a rate of 0.25 to 4.0 kilograms per hectare.
3. Method of claim 1 wherein the triazine is applied at a rate of 0.5 to 1.0 kilograms per hectare.
4. Method of claim 1 wherein the triazine is is applied pre-emergence to plant or stubble cane.
5. Method of claim 1 wherein the triazine is applied post-emergence after top growth of the cane is well started.

* * * * *